United States Patent
Fürnrohr et al.

(10) Patent No.: US 7,289,724 B2
(45) Date of Patent: Oct. 30, 2007

(54) BAG FOR HEATING LIQUIDS AND MEANS FOR HEATING THE BAG

(75) Inventors: Markus Fürnrohr, Stuttgart (DE); Wolfgang Theilacker-Beck, Stuttgart (DE); Matthias Theilacker, Stuttgart (DE)

(73) Assignee: WWT Technischer Gerätebau GmbH, Stuttgart (DE)

( * ) Notice: Subject to any disclaimer, the term of this patent is extended or adjusted under 35 U.S.C. 154(b) by 259 days.

(21) Appl. No.: 11/138,518

(22) Filed: May 26, 2005
(Under 37 CFR 1.47)

(65) Prior Publication Data
US 2006/0000829 A1      Jan. 5, 2006

(30) Foreign Application Priority Data
May 29, 2004   (DE) .................. 10 2004 026 446

(51) Int. Cl.
*A61F 7/00*      (2006.01)
(52) U.S. Cl. ...................... 392/470; 604/114
(58) Field of Classification Search .............. None
See application file for complete search history.

(56) References Cited

U.S. PATENT DOCUMENTS 3,590,215 A * 6/1971 Anderson et al. ........... 392/470
4,167,663 A * 9/1979 Granzow et al. ........... 219/497
4,680,445 A * 7/1987 Ogawa ....................... 392/470
4,847,470 A * 7/1989 Bakke ........................ 392/470
4,994,021 A   2/1991 Smith et al.
5,306,269 A * 4/1994 Lewis et al. ................ 604/403
7,004,196 B2 * 2/2006 Schubmehl et al. ........ 137/574

FOREIGN PATENT DOCUMENTS

DE       1953991       5/1971
EP    1 159 019 B1    11/2002

* cited by examiner

*Primary Examiner*—Thor Campbell
(74) *Attorney, Agent, or Firm*—Walter A. Hackler

(57) ABSTRACT

The invention proposes a liquid heating bag 1, in particular, a blood heating bag and a bag heating means 30 for heating liquids, e.g. cooled blood, which flow through the liquid heating bag 1, to a temperature suitable for transfusion. The liquid heating bag 1 has a flow volume 3 formed by at least two flexible plastic foils which are connected to each other at four delimiting edges 5, 6, 7, 8, wherein the flow volume 3 has a flat, substantially trapezoidal basic shape which is delimited by the delimiting edges 5, 6, 7, 8. An inlet line opening 12 and an outlet line opening 14 are disposed on a first delimiting edge 5, and an insertion tab 15 is disposed on a second delimiting edge 6 opposite to the first delimiting edge 5. The liquid heating bag 1 has a liquid flow guiding seam 20 which is formed by connecting the plastic foils in the region of the flow volume 3. The insertion tab 15 is formed as part of the plastic foils, which projects past the second delimiting edge 6.

8 Claims, 3 Drawing Sheets

BAG FOR HEATING LIQUIDS AND MEANS FOR HEATING THE BAG

BACKGROUND OF THE INVENTION

The invention concerns a bag for heating liquids, in particular, a bag for heating blood, and a bag heating means for heating cooled liquids, e.g. blood, to a temperature which is suitable for transfusion. A blood heating system which consists of a liquid heating bag and a bag heating means of this type is used for heating natural blood for transfusion purposes or for dialysis as well as for transfusion of blood plasma or other liquids.

Blood is usually kept at a temperature of approximately 4° C. Prior to use, the blood must be heated to body temperature of approximately 37° C. The blood which is used for transfusions must have a temperature of at least 28° C. and at most 40° C. In particular, in case of an emergency, the blood must be heated very quickly, since it is not possible to keep heated blood ready for possible emergencies. In case of an emergency, the blood must be heated quickly and also the handling of the blood heating system must be simple and straightforward. The stated temperature conditions must be kept irrespective of the flow rate of the blood through the blood heating system. This flow rate may be up to 5 liters per hour for infusions under pressure. To avoid overheating, the temperature of the bag heating means may only be slightly above the body temperature with the consequence that the bag heating means must provide a large heat exchanging surface to obtain sufficient heating capacity.

Prior art discloses bag heating means of various designs. One can differentiate between bag heating means for inserting a liquid heating bag, having a chamber which can be opened and which is closed during heating of the inserted liquid heating bag, and into which the liquid heating bag is inserted, and bag heating means for inserting a liquid heating bag into a gap formed between two heat exchanger plates which are fixed parallel to each other using fastening means. The bag heating means having a chamber which can be opened are relatively difficult to handle and are therefore suited for use in emergencies only to a limited extent.

A bag heating means for inserting a blood heating bag is disclosed in DE 1953991. This bag heating means comprises heating elements which form two substantially rectangular heat exchanger plates with one flat heat exchanging surface each. The heat exchanging surfaces of the heat exchanger plates are disposed opposite to each other at such a distance that a gap is formed between the heat exchanging surfaces for receiving a blood heating bag. The heat exchanger plates are mounted to each other on a first long side edge of the heat exchanger plates such that the heat exchanging surfaces are fixed parallel to each other. The gap is open along a second long side edge and two narrow side edges of the heat exchanger plates such that a blood heating bag can be introduced, e.g. from the second long side edge, into the gap. The gap has a width of approximately 6 millimeters to prevent compression of the inlet line and outlet line, i.e. to prevent squeezing off the flow. A gap with such a wide opening entails that the volume of the blood in the blood heating bag is also very large, such that the blood may be in contact with the heat exchanging surfaces via the blood heating bag. For dialysis applications, the extracorporeal blood volume must be as small as possible, and for applications as blood heating means, the residual volume remaining in the blood heating bag should be as small as possible to prevent waste of blood. For this reason, the use of this bag heating means is quite limited. The blood heating bag disclosed in DE 1953991 must be inserted into the bag heating means with a predetermined orientation. The use of the blood heating system is prone to errors, in particular, in case of an emergency.

US/2003/0099469A1 describes a further bag heating means for inserting a blood heating bag. This bag heating means comprises a gap between two heat exchanger plates. The gap is closed at two long sides. A blood heating bag is inserted into the bag heating means in a similar manner as a thread is introduced into the eye of a needle, thereby using an insertion tab. The blood heating bag has a flow volume formed from two flexible plastic foils which are connected to each other at four delimiting edges, wherein the flow volume has a flat trapezoidal basic shape which is delimited by the delimiting edges. The blood heating bag also comprises an inlet line opening and an outlet line opening, wherein the inlet line opening and the outlet line opening are disposed at a first delimiting edge, and an insertion tab is disposed at a second delimiting edge opposite to the first delimiting edge. The blood heating bag also comprises a liquid flow guiding seam formed by a connection between the plastic foils in the region of the flow volume. The insertion tab is made from a semi-rigid cardboard material and is mounted to the actual blood heating bag. One disadvantage of this blood heating system is the fact that the blood heating bag is produced from several materials. Production of the blood heating bag therefore requires several processing steps which causes great expense. Moreover, insertion of the blood heating bag into the blood heating means is very complex which consumes valuable time in case of an emergency.

It is the underlying purpose of the invention to provide a liquid heating bag and a bag heating means which eliminate the disadvantages of prior art, and in particular provide quick and straightforward handling.

SUMMARY OF THE INVENTION

This object is achieved by the liquid heating bag and bag heating means of the independent claims. The other claims represent preferred embodiments of the invention.

The inventive liquid heating bag comprises a flow volume formed from at least two flexible plastic foils which are connected to each other at four delimiting edges, wherein the flow volume has a flat, substantially trapezoidal basic shape which is delimited by the delimiting edges. The blood or, in general, the liquid to be heated, may flow through an inlet line opening into the flow volume and can leave the flow volume again through an outlet line opening. The inlet line opening and the outlet line opening are disposed at a first delimiting edge. A liquid flow guiding seam formed by connecting the plastic foils in the region of the flow volume produces a flat flow of the liquid, in particular, of the blood, through the flow volume. An insertion tab is disposed at a second delimiting edge opposite to the first delimiting edge. In accordance with the invention, the insertion tab is designed as part of the plastic foils, which projects past the second delimiting edge. The insertion tab is preferably produced from the same foil as the entire liquid heating bag. The insertion tab permits rapid introduction into a blood heating means. Production of the liquid heating bag is particularly inexpensive, since the entire liquid heating bag is produced from a flexible plastic foil. The inventive liquid heating bag is a disposable bag, i.e. the liquid heating bag is disposed after one-time use. The insertion tab projects only slightly past the flow volume. The liquid heating bag can be folded or rolled together to minimize the size of the aseptic package. That means that the liquid heating bag is flexible, it shows no rigidity, it is not dimensionally stable in its reduced state.

The flow volume is preferably formed by directly welding the plastic foils to each other at the delimiting edges and designing the liquid flow guiding seam as a welding seam between the plastic foils. The liquid heating bag requires no additional reinforcing frame. It consists exclusively of plastic foil. Welding of the foils produces an inexpensive and reliable connection between the foils.

In an advantageous embodiment, the basic shape of the inventive liquid heating bag is elongated, wherein the opposing first and second delimiting edges are designed as narrow sides. The liquid flow guiding seam preferably starts at the first delimiting edge and extends substantially parallel to an upper delimiting edge, formed as long side, thereby dividing the first delimiting edge into an upper and lower section and providing the flow volume with a U shape. In this embodiment, the inlet line opening is disposed in a region of the upper section at the upper delimiting edge and the outlet line opening is disposed in a region of the lower section on the liquid flow guiding seam. The inlet line opening and the outlet line opening are thus each disposed in a corner of the flow volume. The blood which flows through the flow volume is forced to flow through the entire flow volume before it reaches the outlet line opening due to the shape of the liquid flow guiding seam, which provides uniform and quick heating of the blood or liquid. Since the inlet line opening and the outlet line opening are each disposed at one corner of the flow volume, the blood volume which remains in the liquid heating bag e.g. after transfusion, can be minimized by squeezing out the inventive liquid heating bag from a point of the liquid heating bag opposite to these corners, i.e. the residual blood is moved towards the corners.

The first delimiting edge and the upper delimiting edge thereby preferably form an acute angle and the lower section and the liquid flow guiding seam form an acute angle such that the inlet line opening and the outlet line opening are each disposed at the tip of the respective angle. This additionally facilitates "squeezing out" of the residual blood. The residual blood can e.g. be moved into the direction of the outlet line opening such that two parallel heat exchanger plates of a bag heating means compress the bag from the delimiting edge opposite to the upper delimiting edge. The residual blood is discharged to the outlet line opening due to the acute angles.

An inventive bag heating means for inserting a liquid heating bag, preferably in accordance with the invention, comprises heating elements which form two substantially rectangular heat exchanger plates each having a flat heat exchanging surface. The heat exchanger plates are disposed opposite to each other with their heat exchanging surfaces having a mutual distance from each other such that a gap is formed between the heat exchanging surfaces, with a gap width suitable for receiving the liquid heating bag. The heat exchanger plates are mounted to each other on a first long side edge of the heat exchanger plates via fastening means such that the heat exchanging surfaces are fixed substantially parallel to each other via the fastening means. The gap width is thus defined by the design of the fastening means. The gap is open along a second long side edge and two narrow side edges of the heat exchanger plates. The gap of the bag heating means is open to three sides which facilitates insertion of the liquid heating bag and also facilitates cleaning of the gap. In accordance with the invention, the fastening means are resilient such that a pressure change in the liquid heating bag, which is inserted into the bag heating means, caused e.g. through changes in the flow velocity, changes the gap width, wherein a pressure increase widens the gap and pressure reduction reduces the size of the gap. The two heat exchanger plates are flexibly mounted to each other only on one long side which permits simple realization of the pressure-dependent widening and narrowing of the gap width and therefore of the flow volume of a liquid heating bag. The flow cross-section increases with higher flow velocity and associated greater pressure loss in the blood or liquid flow. This is advantageous in that the transfusion is not decelerated by a greater pressure loss, the blood is not harmed by a high flow or flux velocity in the liquid heating bag and the heat transfer from the heat exchanger plates to the heated bag is improved. If the pressure in the flow volume is reduced, i.e. when the transfusion is terminated, decelerated or interrupted, the flow volume is reduced since the gap width automatically decreases in size. Only a small residual volume remains in the liquid heating bag at the end of the treatment. The liquid heating bag, in particular in accordance with the present invention, can be emptied in a simple manner after use, thereby minimizing the amount of residual blood.

The gap width is preferably changed to a gap width of between one and three millimeters. When the liquid heating bag is not inserted or if it is inserted but not pressure-loaded, the gap width is between one and one and a half millimeters which still permits easy introduction e.g. of an inventive liquid heating bag. A gap of this small thickness is obtained in that the inlet line and the outlet line e.g. of the inventive liquid heating bag are disposed on the same side edges of the liquid heating bag. Otherwise, the lines would be disconnected from the heat exchanger plates. The small gap width produces a very small flow volume and therefore provides uniform heating of the blood.

In a further preferred embodiment of the inventive bag heating means, one of the narrow side edges of the heat exchanger plates has two grooved projections. The grooved projections are shaped complementarily to an inlet line opening and an outlet line opening of a liquid heating bag such that the inlet line and the outlet line of the liquid heating bag are positively held in the grooved projections while the liquid heating bag is inserted into the bag heating means. To insert an inventive liquid heating bag into the inventive bag heating means, the liquid heating bag is held with one hand at the insertion tab and with the other hand on the side of the inlet line opening and is inserted into the gap between the heat exchanger plates from the open, long side. Then, the liquid heating bag is slightly pulled e.g. by a few millimeters in the direction of the insertion tab. The inlet line connected to the liquid heating bag and the outlet line are thereby pulled into the grooved projections and positively held in the grooved projections. The inlet line and outlet line are thereby protected from bending.

The invention is explained in more detail below using embodiments and with reference to the drawings.

The figures of the drawings show the inventive object in a highly schematized manner and are not to be taken to scale. The individual components of the inventive object are illustrated such that their construction is clearly shown.

DESCRIPTION OF THE PREFERRED EMBODIMENT

Figure 1:
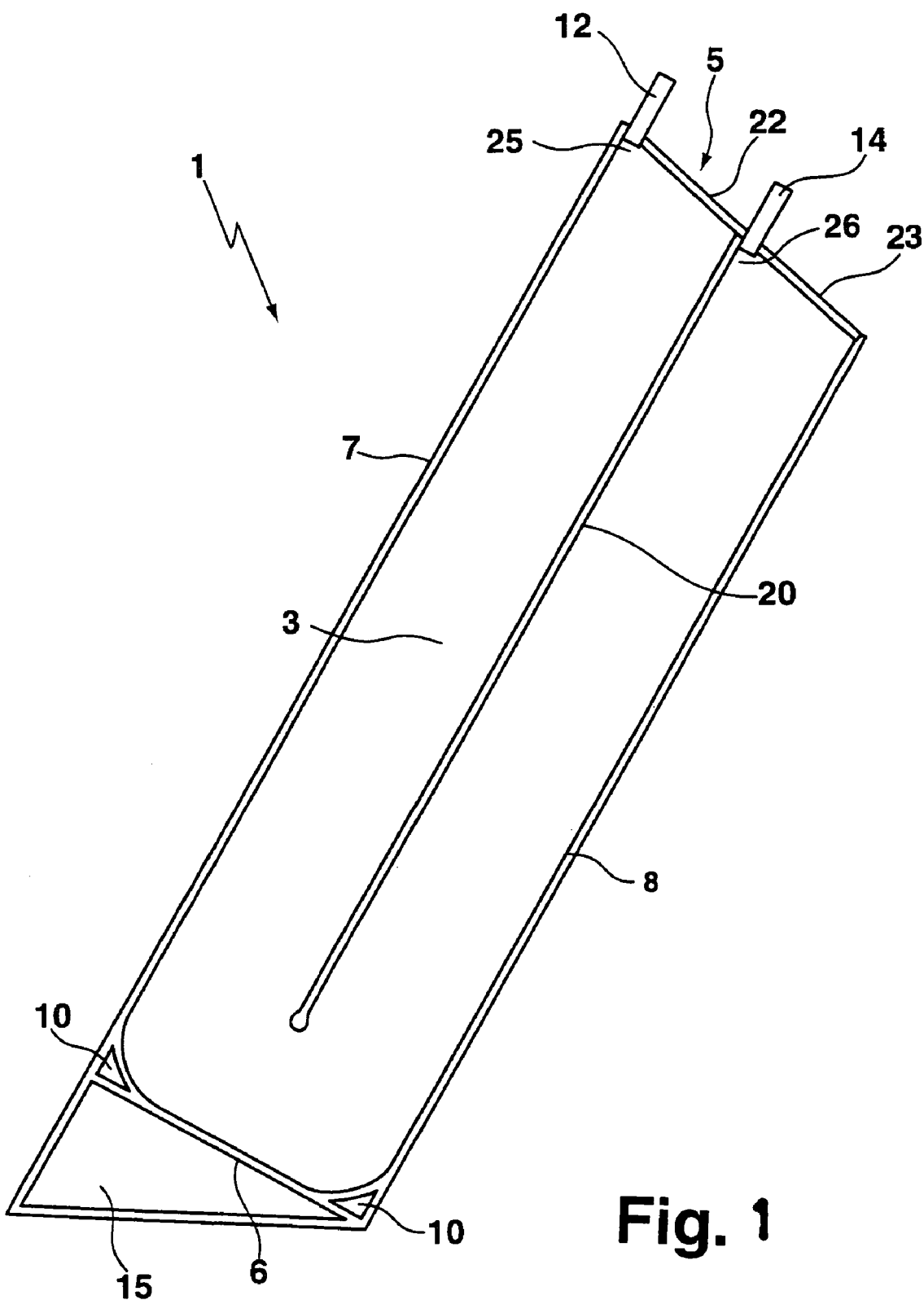
FIG. 1 shows an inventive liquid heating bag.

FIG. 1 shows an inventive liquid heating bag 1. The liquid heating bag 1 has a flow volume 3 which is formed from two flexible plastic foils which are connected to each other at four delimiting edges 5, 6, 7, 8. The flow volume 3 has a flat, substantially trapezoidal basic shape. The corners 10 which are each e.g. formed by two of the delimiting edges 5, 6, 7, 8 may substantially also be rounded. An inlet line opening 12 and the outlet line opening 14 are disposed on the first delimiting edge 5. An insertion tab 15 is disposed on the second delimiting edge 6 opposite to the first delimiting edge 5. The insertion tab 15 is formed as part of the plastic foils, that projects past the second delimiting edge 6. Hence, the liquid heating bag 1 is produced in one piece from one material, i.e. the material of the plastic foils. The basic shape of the liquid heating bag 1 and its flow volume 3 are elongated, wherein the opposing first delimiting edge 5 and the second delimiting edge 6 are formed as narrow sides. A liquid flow guiding seam 20 which is formed by a joint, preferably a welding seam, of the plastic foils in the region of the flow volume 3 starts at the first delimiting edge 5 and extends parallel to the upper delimiting edge 7 formed as long side. The liquid flow guiding seam 20 divides the first delimiting edge 5 into an upper section 22 and a lower section 23. The inlet line opening 12 is disposed in a region of the upper section 22 at the upper delimiting edge 7, and the outlet line opening 14 is disposed in a region of the lower section 22 on the liquid flow guiding seam 20. The first delimiting edge 5 and the upper delimiting edge 7 form an acute angle 25 and the lower section 23 and the liquid flow guiding seam 20 form an acute angle 26 such that the inlet line opening 12 and the outlet line opening 14 are each disposed at the tip of the respective angle 25, 26.

Figure 2A:
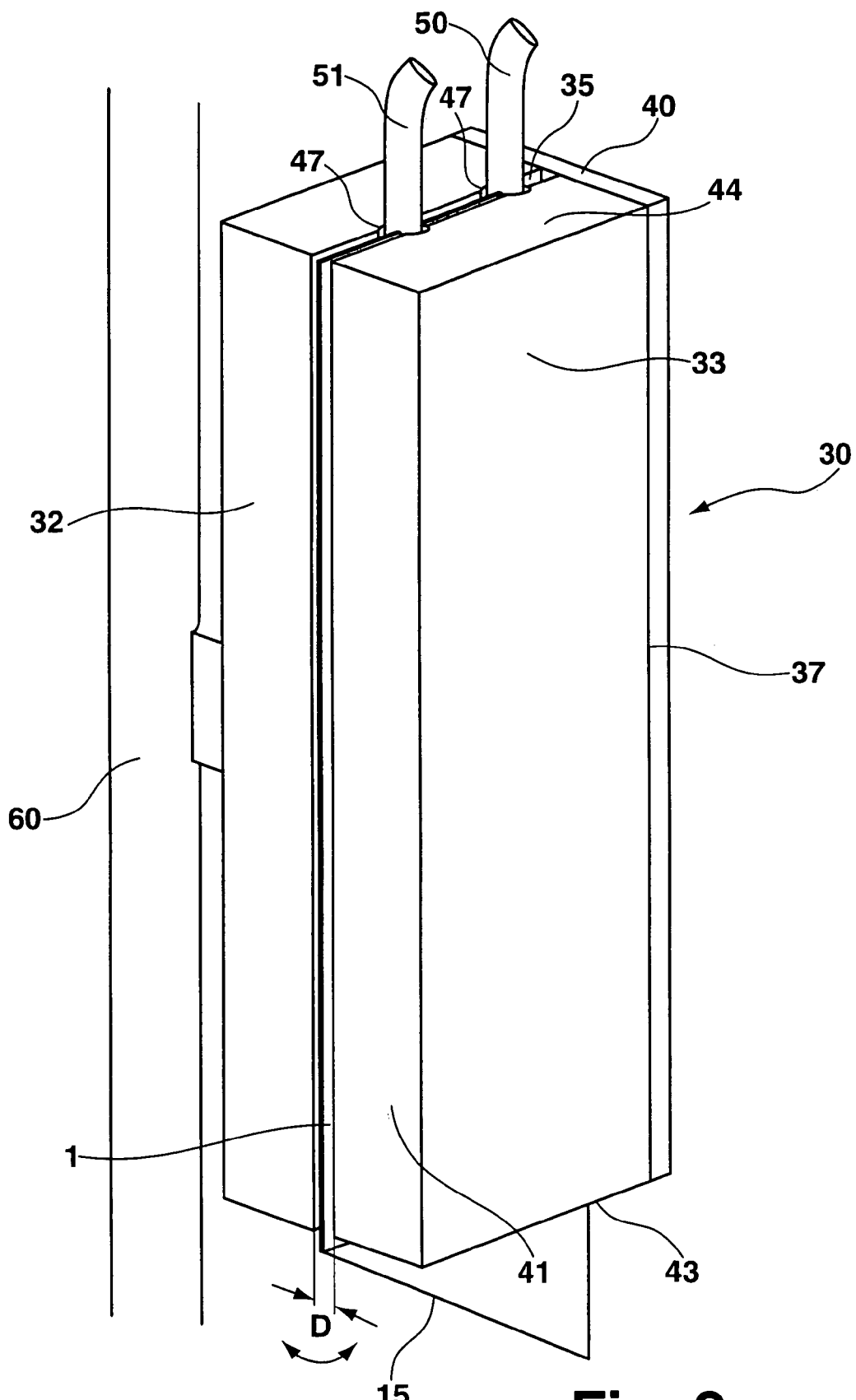
FIG. 2a and FIG. 2b show an inventive bag heating means with an inserted inventive liquid heating bag.
Figure 2B:
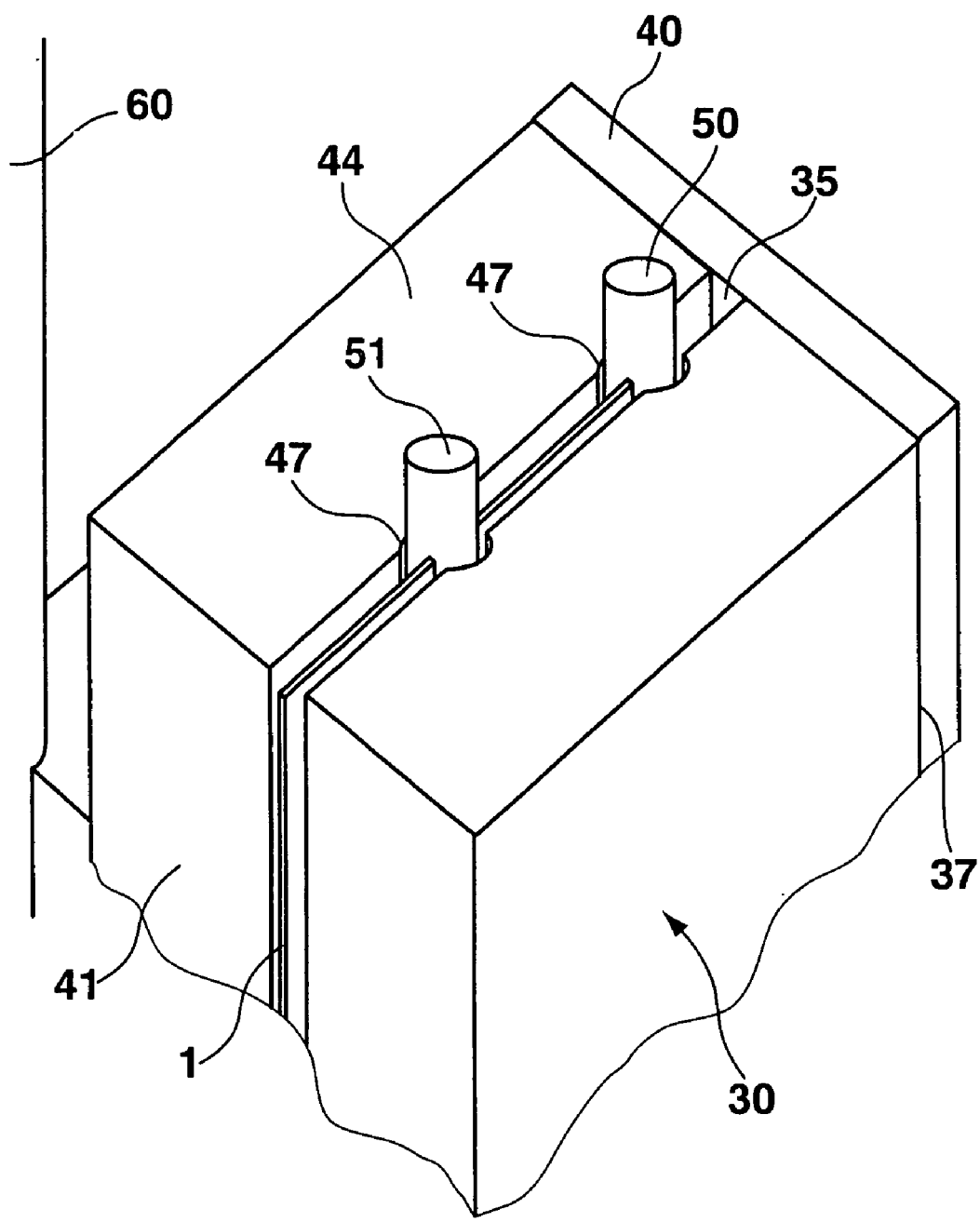

FIGS. 2a and 2b show an inventive liquid heating system, wherein FIG. 2b shows an enlarged section of FIG. 2a. The inventive liquid heating system comprises an inventive bag heating means 30 and an inventive liquid heating bag 1, e.g. a blood heating bag, which is inserted therein. The bag heating means 30 has two heating elements which form two rectangular heat exchanger plates 32, 33 with one flat heat exchanging surface each. The heating elements are preferably electrically heated, wherein a temperature control is provided. The heat exchanger plates 32, 33 are disposed opposite to each other, wherein their heat exchanging surfaces are separated from each other. A gap 35 is formed between the heat exchanging surfaces. The gap width D of the gap 35 is designed to receive an inventive liquid heating bag 1, wherein the insertion tab 15 of the liquid heating bag projects out of the gap 35. The heat exchanger plates 32, 33 are fixed substantially parallel to each other at a first long side edge 37 using fastening means 40. The fastening means 40 are resilient and permit a pressure change in the liquid heating bag 1 inserted into the bag heating means 30, to cause a change in the gap width D, wherein a pressure increase widens the gap 35 and a pressure reduction narrows the gap 35. This property of the inventive bag heating means 30 is indicated in the figure by the bent double arrow. The gap is open along a second long side edge 41 and two narrow side edges 43, 44 of the heat exchanger plates 32, 33 such that a liquid heating bag 1 can be inserted from the second long side edge 41 into the gap 35. The gap width D may thereby vary, preferably between one and three millimeters, depending on the magnitude of the pressure in the inserted liquid heating bag 1, i.e. depending on the pressure exerted by the surfaces of the liquid heating bag 1 onto the heat exchanging surface. The bag heating means 30 has two grooved projections 47 at one of the narrow side edges 44 of the heat exchanger plates 32, 33, wherein the grooved projections 47 are shaped complementarily to the inlet line opening 12 and the outlet line opening 14 of the liquid heating bag 1. An inlet line 50 and an outlet line 51 of the liquid heating bag 1 are thereby positively held in the grooved projections 47 while the liquid heating bag 1 is inserted in the bag heating means 30. The inventive bag heating means 30 is mounted to a mounting rail or an infusion stand. Devices which are commonly used for infusions or transfusions may be disposed on the outlet line extending to the patient. Corresponding examples are a heat clip for a drip chamber, a tube heating or a degassing device.

It is clear that the heat exchanger plates 32, 33 are insulated to the outer atmosphere and are lined with material which is impervious to radiant heat, such that the energy required for heating is almost exclusively transferred to the bag to be heated.

The invention proposes a liquid heating bag 1, in particular, a blood heating bag and a bag heating means 30 for heating liquids, e.g. cooled blood, which flow through the liquid heating bag 1, to a temperature which is suitable for transfusion. The liquid heating bag 1 has a flow volume 3 formed by at least two flexible plastic foils which are connected to each other at four delimiting edges 5, 6, 7, 8, wherein the flow volume 3 has a flat, substantially trapezoidal basic shape which is delimited by the delimiting edges 5, 6, 7, 8. An inlet line opening 12 and an outlet line opening 14 are disposed on a first delimiting edge 5, and an insertion tab 15 is disposed on a second delimiting edge 6 opposite to the first delimiting edge 5. The liquid heating bag 1 has a liquid flow guiding seam 20 which is formed by connecting the plastic foils in the region of the flow volume 3. The insertion tab 15 is formed as part of the plastic foils, which projects past the second delimiting edge 6.

The invention is not limited to the above-mentioned embodiments. A plurality of variants are feasible which utilize the features of the invention even if they have a different basic design.

We claim:

1. A liquid heating bag comprising:
   at least two flexible plastic foils connected to each other at edges to form a flat, substantially trapezoidal flow volume between the edges;
   an inlet line opening and an outlet line opening disposed at a first edge and in fluid communication with the flow volume;
   a liquid flow guiding seam formed by a connection between the plastic foils and disposed within the flow volume;
   an insertion tab, formed as part of the plastic foils, disposed on a second edge opposite the first edge and projecting past the second edge; and
   wherein third and fourth edges of the bag are longer than the first and second edges and the guiding seam extends from the first edge and is generally parallel to the third edge to divide the flow volume into upper and lower sections, the upper and lower sections being in fluid communication with one another proximate the second edge, the inlet line opening being in fluid communication with the upper section and the outlet line opening being in fluid communication with the lower section.

2. The liquid heating bag according to claim 1 wherein the edges and guiding seam are formed by welding the plastic foils together.

3. The liquid heating bag according to claim 1 wherein the first edge and the third edge form an acute angle with one another, the guiding seam and the first edge form an acute angle with one another and the inlet line and outlet line openings are disposed at respective tips of the acute angles.

4. A liquid heating bag comprising:
- at least two flexible plastic foils connected to each other at edges to form a flat, substantially trapezoidal flow volume between the edges;
- an inlet line opening and an outlet line opening disposed at a first edge and in fluid communication with the flow volume;
- a liquid flow guiding seam formed by a connection between the plastic foils and disposed within the flow volume;
- an insertion tab, formed as part of the plastic foils, disposed on a second edge opposite the first edge and projecting past the second edge;
- two substantially rectangular heat exchange plates disposed opposing one another with a gap therebetween suitable for receiving the liquid heating bag;
- mounting means fastened to each of the plates along a long edge thereof for supporting the plates with the gap being open along an opposite long edge and opposing short edge of the plastic, said mounting means being resilient in order that a pressure change in the liquid heating bag disposed within the gap changes a gap width, a pressure increase widening the gap width and a pressure reduction reducing the gap width; and wherein third and fourth edges of the bag are longer than the first and second edges and the guiding seam extends from the first edge and is generally parallel to the third edge to divide the flow volume into upper and lower sections, the upper and lower section being in fluid communication with one another proximate the second edge, the inlet line opening being in fluid communication proximate the second edge, the inlet line opening being in fluid communication with the upper section and the outlet line opening being in fluid communication with the lower section.

5. The liquid heating bag according to claim 4 wherein the edges and guiding seam are formed by welding the plastic foils together.

6. The liquid heating bag according to claim 4 wherein the first edge and the third edge form an acute angle with one another, the guiding seam and the first edge form an acute angle with one another and the inlet line and outlet line opening are disposed at respective tips of the acute angles.

7. The bag heater apparatus according to claim 4 wherein the gap width is variable between one and three millimeters.

8. The bag heater apparatus according to claim 4 wherein each of the heat exchanges plates include grooves therein for guiding and holding inlet and outlet lines connected to the bag.

* * * * *